Figure 4:
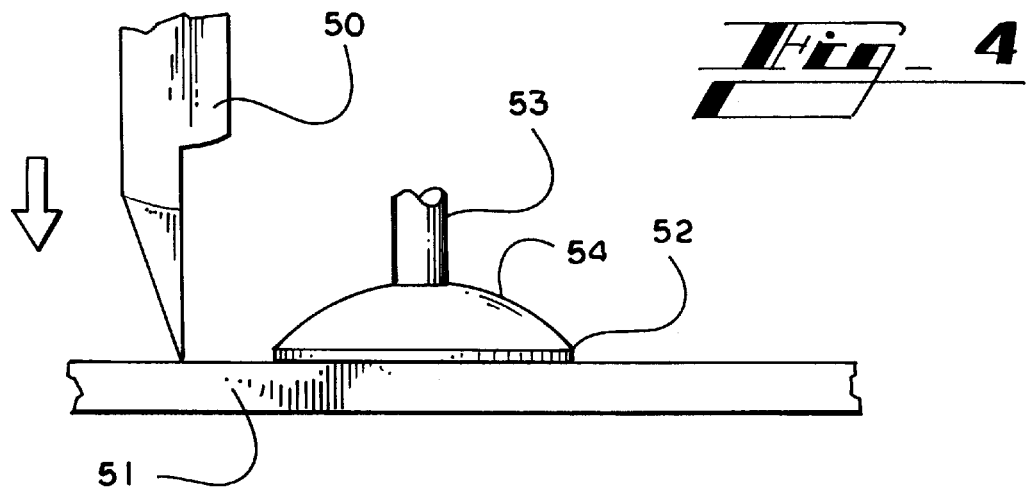

United States Patent [19]
Sykes

[11] Patent Number: 6,078,387
[45] Date of Patent: Jun. 20, 2000

[54] TEST APPARATUS

[75] Inventor: Robert Sykes, Tendring, United Kingdom

[73] Assignee: Dage Precision Industries, Ltd., Buckinghamshire, United Kingdom

[21] Appl. No.: 09/197,106

[22] Filed: Nov. 20, 1998

[30] Foreign Application Priority Data

Nov. 20, 1997 [GB] United Kingdom .................. 9724457

[51] Int. Cl.[7] ................................................. G01N 21/00
[52] U.S. Cl. .......................................... 356/244; 356/213
[58] Field of Search .................................. 356/213, 244

[56] References Cited

U.S. PATENT DOCUMENTS

| 4,531,909 | 7/1985 | Takeshita ................................. 432/37 |
| 5,774,209 | 6/1998 | Shestock ................................. 356/244 |

*Primary Examiner*—Frank G. Font
*Assistant Examiner*—Reginald A. Ratliff
*Attorney, Agent, or Firm*—Jones & Askew

[57] ABSTRACT

Apparatus for testing electrical bonds of a semiconductor device includes a cantilever arm (14*a*) with a test head (16) mounted thereon. The test head (16) is biased by the arm (14*a*) against a base plate (11), but can be moved away from the base plate (11) by an air bearing (22) to ensure substantially frictionless initial positioning. Sensing means (32;34) for sensing contact with a semiconductor substrate are also disclosed.

14 Claims, 2 Drawing Sheets

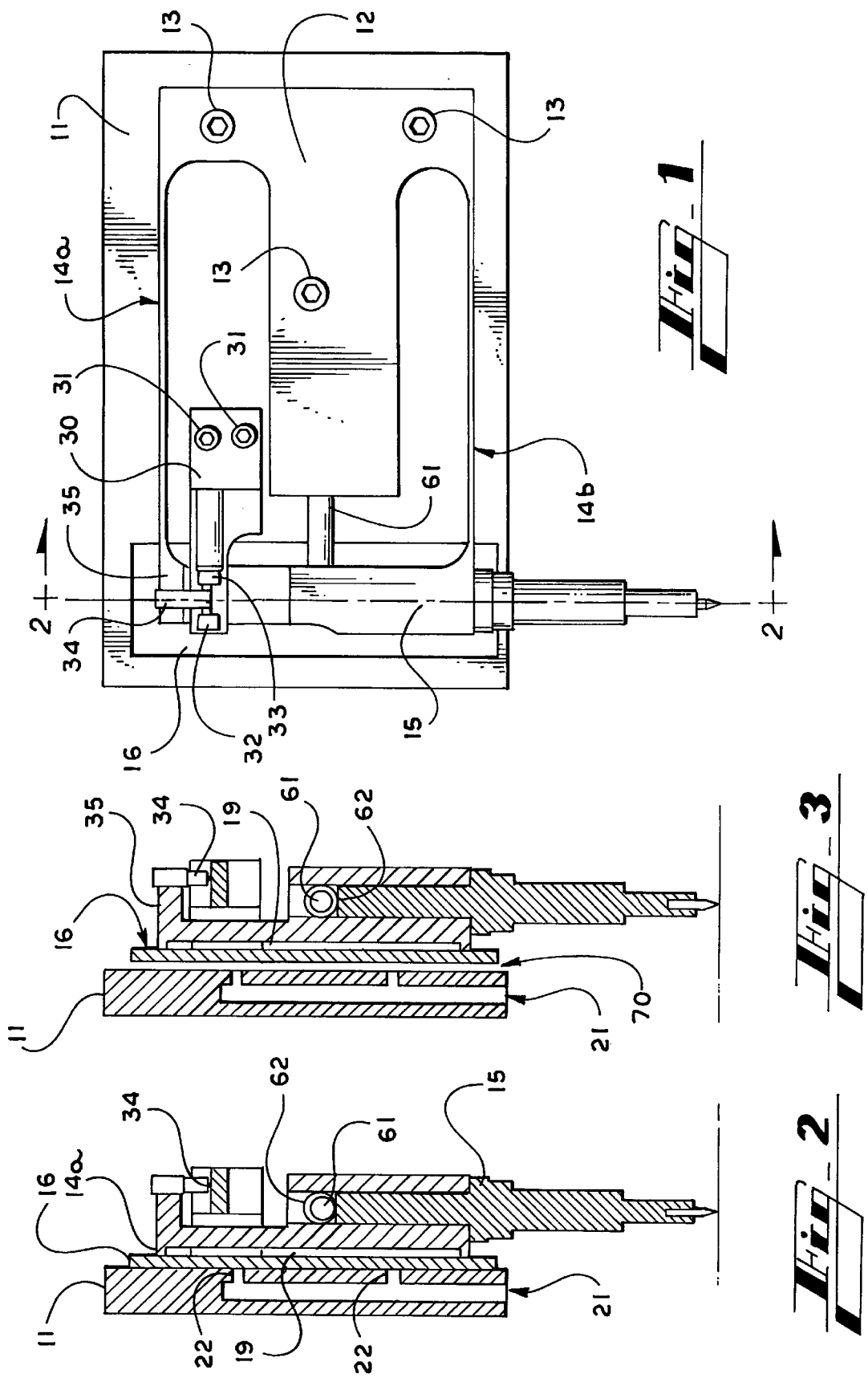

TEST APPARATUS

This invention concerns a device for clamping a test head to a substrate, and also to a device for sensing contact of a test head with a substrate. Such a device is for use particularly with apparatus for testing the integrity of a bond between a semiconductor device and an electrical conductor thereof.

Semiconductor devices are very small, typically from 0.2 mm square to 15 mm square. Around the edge of the semiconductor substrate numerous sites for the bonding of electrical conductors are provided; these sites are typically about 0.05 mm wide and 0.1 mm to 0.7 mm apart. Very thin wires, usually about 0.025 mm in diameter, are bonded to respective sites, and connect these sites to associated electrical circuitry and components. It is necessary to test the bond integrity at the sites in order to gain confidence that the bonding method is adequate and that the bond strength is sufficient. Difficulties arise because of the very small dimensions of the components, the precision with which the testing device must be positioned, and the very small forces and deflections which are to be measured.

A known test apparatus has a probe for engagement with the wire bond at a respective site. The semiconductor device is restrained and the wire bond pushed sideways by the probe to determine the bond shear strength. A force transducer is incorporated in the device to measure the force necessary to shear the bond.

In order to ensure repeatability it is essential for the probe to engage the side of the bond at a predetermined height above the surface of the semiconductor. This distance is small but critical since the bond is usually domed. A predetermined spacing from the surface both eliminates sliding friction from the probe on the semiconductor substrate, and ensures that the shear load is applied at a precise location in relation to the bond interface. Accordingly, in practice, the probe is moved into engagement with the semiconductor surface, and then withdrawn by a predetermined amount, typically 0.05 mm or less, before being moved sideways into contact with the bond site.

Several difficulties arise. Friction and stiction in the mechanism of the device itself may cause difficulties in sensing contact with the semiconductor surface; imprecise surface sensing will inevitably affect the distance by which the probe is withdrawn, and thus the height at which the bond is tested. The distances involved are very, very, small and thus every care needs to be taken to sense the exact moment of surface contact without compression of the semiconductor substrate. Care must also be taken to prevent uncontrolled movement of the probe at the test height, and prior to the application of the shear test force; such movement may again seriously affect the test result, and significant movement of the probe may damage an adjacent bond or wire.

The objectives of a low contact force when sensing the semiconductor substrate, and accurate control of test height are difficult to resolve.

According to a first aspect of the invention there is provided a clamping device for a test head mounted on a base plate by a cantilever arm, wherein the test head is biased into engagement with said base plate by said arm, and an air bearing is provided operatively between said test head and base plate, the air bearing being operable to urge said test head out of engagement with said base plate. Preferably the air bearing includes one or more ducts in said base plate for supplying air under pressure, a chamber on the underside of said test head, and a plurality of supply ports opening from said base plate into said chamber.

Preferably the test head is mounted on two cantilever arms extending in substantially the same direction. Such an arrangement is particularly stable.

In a preferred embodiment the biasing force of the arm or arms is just sufficient to prevent relative movement of said test head, and the force generated by the air bearing is just sufficient to move said test head out of engagement with the base plate. Such an arrangement permits the test head to be securely held at the desired test height, and thereby prevents uncontrolled test head movement.

According to a second aspect of the invention there is provided a device for sensing contact of a test head with a substrate and comprising a base plate having two cantilever arms extending in substantially the same direction therefrom, a test head operatively fixed to the free ends of said arms, said base plate having detecting means thereon for sensing movement of said test head relative to said base plate in the plane of said arms, and a support being provided between said test head and base plate whereby a proportion of the mass of said test head is carried by said base plate via said support. Preferably the support is adjustable.

The advantage of supporting a proportion of the mass of the test head on the base plate is that touchdown of the test head on a substrate is more gentle, and can thus be sensed before a significant load is exerted on the substrate. Early sensing also permits the downwards drive of an automated test machine to be stopped before a significant load is exerted on the substrate.

Preferably the position of the test head is monitored, by e.g. a photo emitter and photo detector. In the preferred embodiment the photo emitter and detector monitor separation of an edge of the test head from the base plate. The support may be a stud screw-threaded in the test head and providing an edge for the photo-detector.

Other features of the invention will be apparent from the following description of a preferred embodiment illustrated by way of example only in the accompanying drawings, in which FIG. 1 is a side elevation of a device according to the present invention.

FIG. 2 is a section on line X—X of Fig illustrating the passive condition.

FIG. 3 corresponds to FIG. 2 and shows the active condition.

Figure 5:
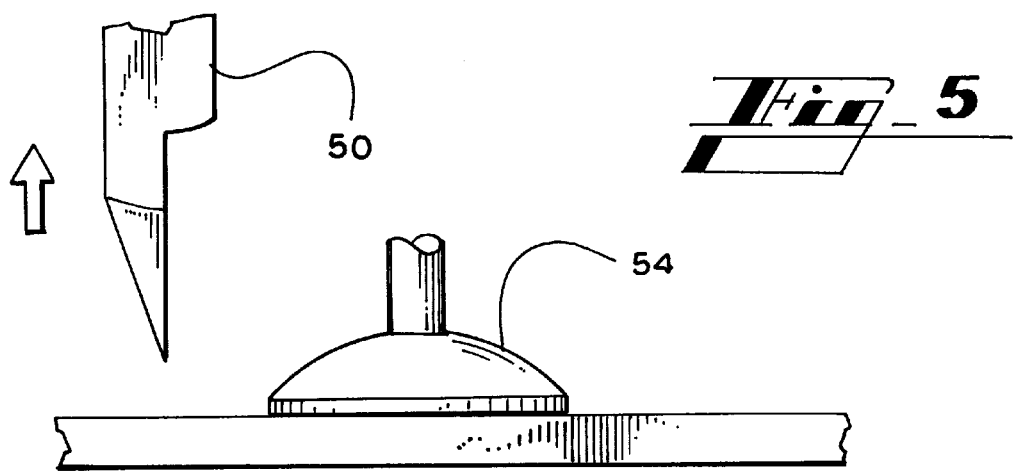
Figure 6:
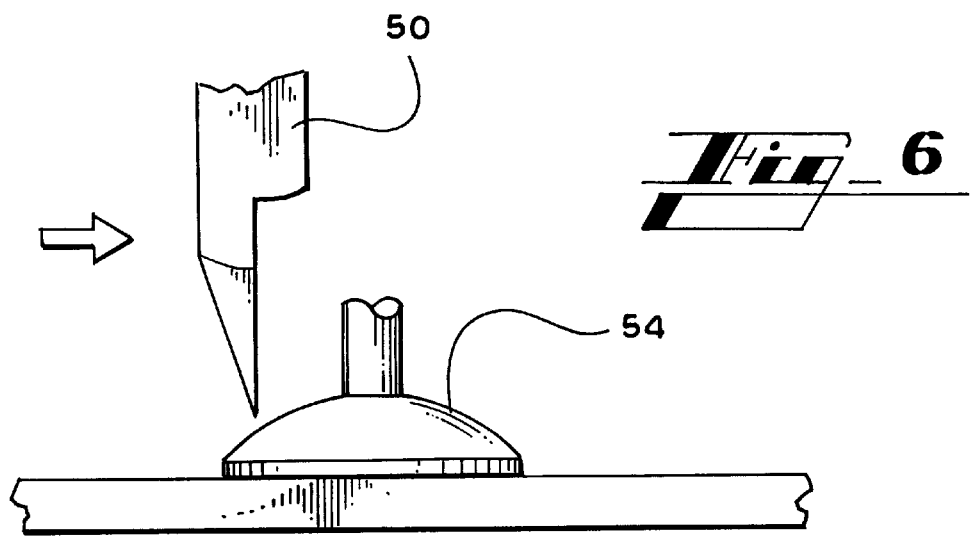

FIGS. 4–6 illustrate stages in the movement of the device.

A transducer cartridge 10 comprises a base plate 11 to which is rigidly attached a fixed mass 12 by screws 13. The fixed mass has upper and lower cantilever arms 14a, 14b to the free ends of which are attached a moving mass 15. The cantilever arms 14a, 14b permit up and down movement of the moving mass 15, and together determine the rest position of the moving mass 15.

The inner sides of the free ends of the arms 14a, 14b carry a bearing plate 16 which itself lies against the base plate 11. In the rest position the arms 14a, 14b are arranged to exert a bias force towards the base plate 11 which is just sufficient to clamp the bearing plate 16 and thus prevent oscillation of the moving mass 15 in the up and down direction. This bias force ensures that the moving mass 15 does not move relative to the base plate 11 whilst the base plate is itself being moved.

The base plate 11 includes air bearing 20 comprising an air supply duct 21 having outlet ports 22 to a chamber 19 on the underside of the bearing plate 16. The supply of air under pressure to the duct 21 causes the bearing plate 16 to move away from the base plate 11, against the bias force of the arms 14a, 14b, and thus permits friction free movement of the moving mass in the up and down direction.

The bias force and the degree of air pressure required to overcome it is a matter of detailed design, and can be determined by the skilled man according to the test requirements. Likewise, the area of engagement of the arms 14a, 14b on the bearing plate 16, the area of engagement of the bearing plate 16 on the base plate 11, the air porting arrangement and other variable factors may be determined according to particular circumstances. Generally speaking the bias force should be just sufficient to restrain movement of the moving mass 15 whilst performing a test, and the air pressure should be just sufficient to allow the moving mass 15 to move freely.

A travel sensor mount 30 is fixed to base plate 11 by screws 31. The mount 30 has a photoelectric emitter 32 and receiver 33 between which extends a stud 34 which is screw-threaded in a projection 35 of the upper cantilever arm 14a. As illustrated in FIG. 1, the stud 34 can be screwed into engagement with the mount 30 and thereby jack the moving mass 15 upwards relative to the base plate 11. This arrangement permits an adjustment of the proportion of the actual mass of the moving mass 15 which is carried the arms 14a, 14b and which is carried by the stud 34, when the air bearing is active. This ensures that the lightest of contacts by the probe tip causes slight upward movement of the probe, and thereby changes the degree with which the stud 34 obscures the light path between emitter 32 and receiver 33. Typically the initial contact force of the probe tip is in the range 0–50 g, for example 15 g, but can be adjusted according to the projection of the stud 34.

This load sharing arrangement alleviates the problem that the actual mass of the moving mass 15 may be sufficient to indent the surface 40 of the semiconductor 41 or that the apparatus moving the probe into contact with the surface 40 may embed the probe in the surface before downwards drive ceases. Inevitably there is a small but finite time for the contact to be sensed, and for the Z axis drive to stop. The present arrangement allows the point of contact to be sensed with considerable precision since movement of the moving mass 15 is free of friction and the photoelectric sensor 32, 33 can detect small changes in the degree of light transmitted. The time taken for the Z axis drive to stop can be related to a precise distance, and consequently an allowance can readily be made in the distance through which the probe is withdrawn prior to test.

A projection 61 of the base plate is loosely located in an aperture 62 of the test head, and serves to restrict movement of the arms 14a, 14b to their elastic range.

Stages of use of the device are illustrated in FIGS. 4–6 which show a probe tip 50, semiconductor substrate 51, electrical contact 52, electrical wire 53 and bond 54.

The precise shape of the bond 54 may vary due to production techniques, and consequently the bond shown in FIGS. 4–6 is for illustration purposes only.

In use air pressure is applied and the moving mass is supported by elastic deflection of the arms 14a, 14b. At this stage the proportion of the load taken by the stud 34 can be adjusted to give the desired touch down load. It should not be necessary to adjust the stud after initial setting unless test conditions are changed. Then, the back plate 11 is driven towards the substrate 51 until the probe tip 51 is close to the test site; the actual mass of the moving mass 15 is not so great as to oscillate under rapid movement of the base plate.

Just above the substrate movement of the back plate is slowed until contact is sensed by the optical sensors 32, 33 (FIG. 4). The gap 70 created at the air bearing is exaggerated in FIG. 3; in practice air pressure will be selected to ensure that the arms 14a, 14b just separate from the back plate 11.

Once contact is sensed, travel of the back plate ceases. The air supply to the bearing also ceases, and as a consequence the beams move imperceptibly to engage the back plate (FIG. 2). At this stage the moving mass 15 is held firmly relative to the back plate by the inherent sideways spring force generated by the beams 14a, 14b. Slight residual load in the beams 14a, 14b may also be retained by this inherent spring force. Movement due to ceasing of the air supply is solely in the direction of the collapsing air gap, and the probe tip maintains light contact with the substrate surface.

The back plate is then retracted by a predetermined amount (FIG. 5) and moved laterally against the bond (FIG. 6) to commence the shear test.

In practice drive of the back plate is automated to ensure repeatability of test conditions. Positioning of the probe in the vicinity of a bond to be tested is typically carried out manually using magnifying techniques, or by pre-programming if a datum and bond site spacing are known.

Several different test heads may be provided, each designed according to the range of applied loads. Typically test heads adapted to apply nominal loads of 250 g, 5 kg and 100 kg may be provided.

The apparatus has no internal moving parts and indeterminate friction and stiction forces are eliminated.

What is claimed is:

1. A clamping device for a test head and comprising a base plate, a resilient cantilever arm extending from the base plate, the cantilever arm having a free end movable towards and away from said base plate, a test head on said free end, said test head being biased into engagement with said base plate by said arm, and an air bearing being provided operatively between said test head and base plate, the air bearing being operable to urge said test head out of engagement with said base plate against said bias.

2. A device according to claim 1 wherein said air bearing includes one or more ducts in said base plate for supplying air under pressure, a chamber on the underside of said test head, and a plurality of supply ports opening from said base plate into said chamber.

3. A device according to claim 1 wherein said test head is mounted on two cantilever arms extending in the same direction.

4. A device according to claim 3 wherein said arms are of equal length.

5. A device according to claim 2 wherein said test head is mounted on two cantilever arms extending in the same direction.

6. A device according to claim 5 wherein said arms are of equal length.

7. A clamping device for a test head and comprising a base plate, a cantilever arm extending from the base plate, and test head on the free end of said cantilever arm, said test head being biased into engagement with said base plate by said arm, an air bearing provided operatively between said test head and base plate, the air bearing being operable to urge said test head out of engagement with said base plate, and further including sensing means for sensing contact of said test head with a substrate, said base plate having detecting means thereon for sensing movement of said test head in a direction perpendicular to the line of action of said air bearing, and a support being provided between said test head and base plate whereby a proportion of the mass of said test head is carried by said base plate via said support.

8. A device according to claim 7 wherein said support is adjustable to vary the proportion of mass supported thereon.

9. A device according to claim 7 wherein said sensing means comprises a photo emitter and photo detector.

10. A device according to claim 8 wherein said sensing means comprises a photo emitter and photo detector.

11. A device according to claim 9 wherein said photo emitter and detector monitor separation of an edge of test head from an abutment of said base plate.

12. A device according to claim 10 wherein said photo emitter and detector monitor separation of an edge of test head from an abutment of said base plate.

13. A device according to claim 11 wherein said support comprises a stud screw-threaded in the test head and providing said edge for the photo-detector.

14. A device according to claim 12 wherein said support comprises a stud screw-threaded in the test head and providing said edge for the photo-detector.

* * * * *